(12) United States Patent
Prime et al.

(10) Patent No.: US 6,175,984 B1
(45) Date of Patent: Jan. 23, 2001

(54) APPARATUS FOR CLEANING PRECISION COMPONENTS

(75) Inventors: Robert Bruce Prime; Ronald Lee Weaver, both of San Jose, CA (US)

(73) Assignee: International Business Machines Corporation, Armonk, NY (US)

( * ) Notice: Under 35 U.S.C. 154(b), the term of this patent shall be extended for 0 days.

(21) Appl. No.: 08/922,164

(22) Filed: Sep. 2, 1997

(51) Int. Cl.$^7$ .................................................. A47L 25/00
(52) U.S. Cl. .................................. 15/104.002; 15/209.1; 15/210.1; 15/DIG. 13
(58) Field of Search ......................... 15/104.002, 209.1, 15/210.1, DIG. 13; 294/1.1

(56) References Cited

U.S. PATENT DOCUMENTS

| | | | |
|---|---|---|---|
| 3,797,875 | 3/1974 | den Hamer | 294/1.1 |
| 3,864,993 | 2/1975 | Hovind | 81/488 |
| 3,920,877 | * 11/1975 | Barber et al. | 427/505 |
| 3,958,292 | * 5/1976 | Powell | 15/104.002 |
| 4,073,530 | 2/1978 | Seidler | 294/19.1 |
| 4,128,909 | * 12/1978 | Kawabe et al. | 15/104.002 |
| 4,158,871 | 6/1979 | Leaming | 360/137 |
| 4,306,555 | 12/1981 | Ritter | 19/145.3 |
| 4,329,753 | * 5/1982 | Weil | 15/104.002 |
| 4,727,616 | * 3/1988 | Kucera et al. | 15/104.002 |
| 4,902,368 | * 2/1990 | Oldham | 156/306.9 |
| 5,109,637 | 5/1992 | Calafut | 451/495 |
| 5,181,755 | 1/1993 | Stanwich et al. | 294/1.1 |
| 5,195,278 | 3/1993 | Grove | 451/524 |
| 5,239,723 | * 8/1993 | Chen | 15/104.002 |
| 5,251,943 | 10/1993 | Dalbo et al. | 294/1.1 |
| 5,417,743 | * 5/1995 | Dauber | 96/13 |
| 5,435,328 | * 7/1995 | Grohoske | 15/104.002 |
| 5,470,116 | 11/1995 | DeWoskin | 294/1.1 |
| 5,525,059 | 6/1996 | Lee | 433/141 |
| 5,585,981 | 12/1996 | Lee | 360/106 |
| 5,765,887 | * 6/1998 | Weichman et al. | 294/1.1 |
| 5,811,184 | * 9/1998 | Anderson et al. | 428/343 |
| 5,940,921 | * 8/1999 | Wood et al. | 15/104.002 |

FOREIGN PATENT DOCUMENTS 2164881A 4/1986 (EP) .

OTHER PUBLICATIONS

"Cleaning Stick", IBM Technical Disclosure Bulletin, vol. 30, No. 7, Dec. 1987, p. 418.

* cited by examiner

Primary Examiner—Robert J. Warden, Sr.
Assistant Examiner—Theresa T. Snider
(74) Attorney, Agent, or Firm—Noreen A. Krall; Randall J. Bluestone

(57) ABSTRACT

A cleaning apparatus for cleaning sensitive components such as those used in the disk drive and semi-conductor industries. The cleaning apparatus of the present invention includes of an adhesive tip mounted on a handle. The adhesive tip may be fixedly or rotatably mounted on the handle, and is further comprised of an adhesive film which may be wrapped about the handle or formed over a more compliant or more resilient surface. The adhesive film is preferably a low residue, low out gassing material which may easily remove particles from the surface of precision components without further contaminating the component.

18 Claims, 5 Drawing Sheets

APPARATUS FOR CLEANING PRECISION COMPONENTS

CROSS REFERENCE TO RELATED APPLICATIONS

The present invention is related to application Ser. No. 08/922,101 entitled Method for Manufacturing a Cleaning Apparatus for Cleaning Precision Components filed Sep. 2, 1997.

BACKGROUND OF THE INVENTION

1. Field of the Invention

The present invention relates in general to the cleaning of precision components, and more particularly to a cleaning apparatus and method of use particularly suited for cleaning precision components without leaving harmful residue on the component surface.

2. Description of the Related Art

One problem which affects manufacturers of precision components such as medical instruments, electronic components, disk drive systems, etc. is particulate contamination of the device or component. In particular, the manufacturers, service providers or users of these devices need a cleaning apparatus and method for using that allows the operator to easily remove particles from the surface of these parts or devices. Typically, these components cannot be washed in aqueous or solvent cleaners, and the only way to remove the particles is by wiping the components with cloths or swabs, which is inefficient and relatively ineffective.

One approach found in the prior art to address these problems is the gumstick described in IBM Technical Disclosure Bulletin Vol. 30, No. 7. The cleaning or gumstick described includes an acrylic rod with a rubber based transfer material. The problem with this approach, however, is that the transfer material itself may contaminate the device it is intended to clean. Although the existing particles on the component are lifted by the gumstick, a harmful residue may be left behind which may adversely affect the operation of the component. For example, in a disk drive system, the gumstick could leave a residue on the component that would volatilize by heating of the component during operation of the disk drive and subsequently condense on the surface of the disk where the temperature is cooler. This effect, referred to as outgassing, can lead to a head crash in operation of a disk drive system.

Other small object pick up devices found in the prior art include U.S. Pat. No. 5,251,943 issued to Dalbo et al., and U.S. Pat. No. 5,470,116 issued to DeWoskin which describe various devices for handling small components. However, these devices are not suited for use in cleaning precision components where the degree of cleanliness is of critical importance.

As can readily be seen there is a need for a cleaning apparatus that is particularly useful for cleaning precision components without leaving harmful residue on the surface of the component. It can further be seen that the apparatus should be simple to manufacture, has to be adequately packaged to avoid contamination before use, and should be able to conform in size and shape based on the component or device to be cleaned.

For the foregoing reasons, it becomes necessary to engineer a new apparatus for addressing the problems of cleaning precision components without further complications arising from harmful residue left behind by the cleaning apparatus.

SUMMARY OF THE INVENTION

To overcome the shortcomings of the prior art, it is the object of the present invention to provide a cleaning apparatus particularly suited for cleaning precision components such as those found in the electronics, disk drive and medical instruments industry.

In accordance with the preferred embodiment of the present invention, the cleaning apparatus of the present invention is comprised of an adhesive tip mounted on a handle. The adhesive tip may be fixedly or rotatably mounted on the handle, and is further comprised of an adhesive film which may be wrapped about the handle or an adhesive layer formed over a more compliant or more resilient surface. The adhesive is preferably a low residue, low out gassing material which may easily remove particles from the surface of precision components without further contaminating the component.

In one embodiment of the present invention, the cleaning apparatus is manufactured by winding or rolling the thin film adhesive material onto a non-particulating dowel similar to a swab handle. In another embodiment, the film may be applied over a compliant surface attached to the end of the handle, or alternatively a more resilient surface on the end of the handle. The adhesive may also be applied directly to a substrate while it is still in a liquid, uncured state.

Optionally, the surface of the adhesive tip of the cleaning apparatus may be cross-linked to further reduce the possibility of residue.

Once manufactured, the adhesive tip of the cleaning apparatus has to be protected prior to use. In one embodiment, a coated Mylar or similar release film would be used to protect the adhesive prior to use. The choice of the release film is critical to avoid siloxane (methyl silicone) contamination.

These and various other advantages and features of novelty which characterize the present invention are pointed out with particularity in the claims annexed hereto and form a part hereof. However, for a better understanding of the invention, its advantages, and the objects obtained by its use, reference should be made to the drawings which form a part hereof, and to the accompanying descriptive matter, in which there is illustrated and described specific examples of a system and method in accordance with the present invention.

BRIEF DESCRIPTION OF THE DRAWINGS

FIG. 1b is a cross-sectional view of the cleaning apparatus of the present invention taken along lines A–A' in FIG. 1a;

DETAILED DESCRIPTION OF THE PREFERRED EMBODIMENTS

Figure 1A:
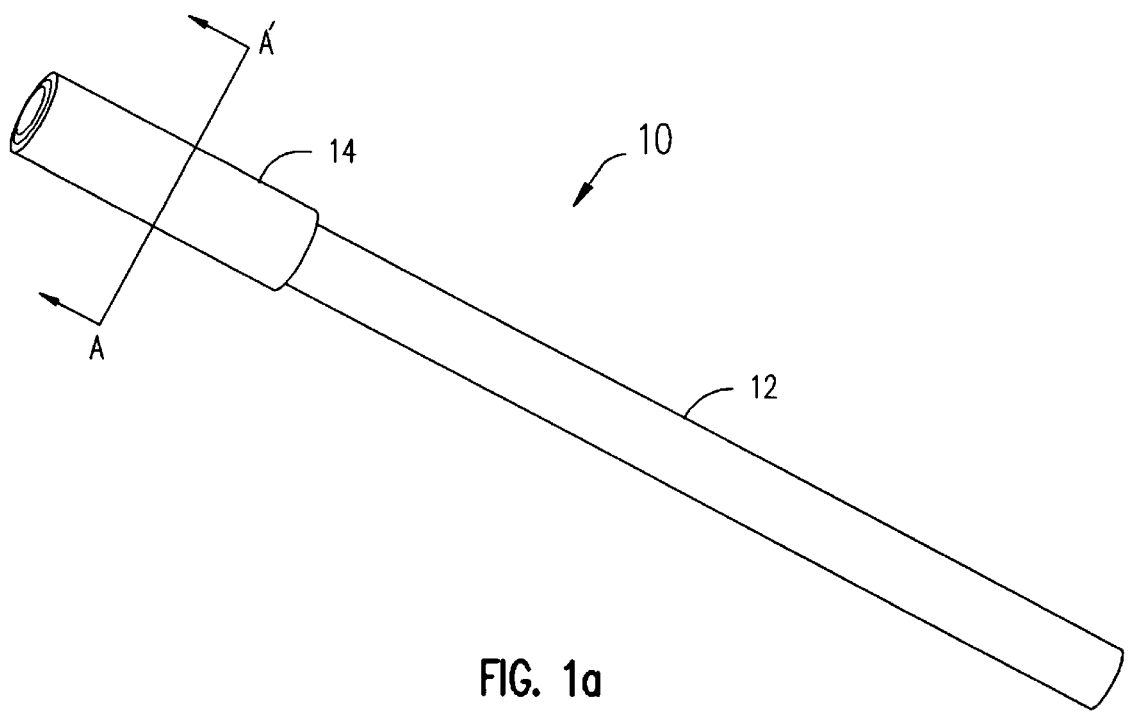
FIG. 1a is a perspective view of the cleaning apparatus of the present invention.

FIG. 1a illustrates a perspective view of the cleaning apparatus 10 of the present invention. As seen in FIG. 1a, the cleaning apparatus 10 comprises a handle 12 and an adhesive tip 14. Adhesive tip 14 may be fixedly or rotatably attached to handle 12. Handle 12 may be round or flat to be suited for use in areas of varying heights or sizes. In addition, handle 12 may be stiff which would be more suited for use in cleaning distant or hard to reach places, or the handle 12 may be flexible to reach around angles in a precision component. In one embodiment, handle 12 is comprised of a non-particulating dowel similar to a swab handle.

Still referring to FIG. 1a, in this first embodiment, adhesive tip 14 is formed using a low residue adhesive material 20 with low outgassing properties. Accordingly, the cleaning apparatus 10 could be used to remove particles from electronics components, medical instruments and the like without leaving behind undesirable and harmful residue on these components. The adhesive used must have sufficient tackiness to remove very small particles from the surface of a component without leaving a residue of any significant amount. The adhesive should also have very low outgassing properties and leave minimal residue so as not to contaminate the part being cleaned and cause problems in the operation of the mechanism in which it is used. In one example relating to the disk drive industry, the adhesive material 20 should have the following properties:

(1) a probe tack as measured by ASTM method D2979 should be greater than 500 grams;

(2) organic volatile outgassing should be less than 0.5%;

(3) no visible residue on separation of the film; and (4) less than $0.1 \mu g/cm^2$ residue from cleaning. One example of such an adhesive material is Arclad AS 123, manufactured by Adhesives Research Corp. Similar adhesives, for example from 3M and Nitto-Denko, have similar acceptable properties. This material typically comes in a thin film 20, which could be applied by winding or rolling it onto the handle 12 as is seen with reference to FIG. 1b. In this embodiment, the round configuration of the adhesive tip 14 would allow the adhesive tip 14 to be rolled across a flat surface during use in a continuous motion, lifting particles from that surface in a controlled manner. This method would be especially useful in cleaning finished, magnetized voice coil motors or disk drive motor assemblies.

Figure 1B:
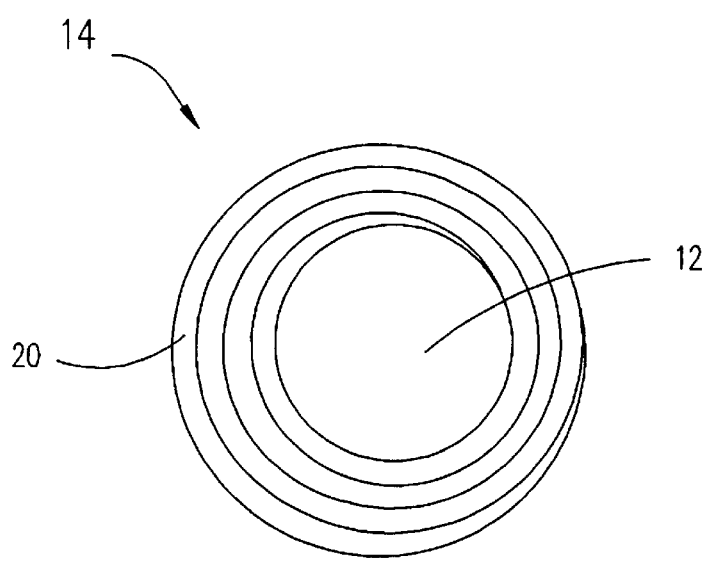
Figure 2A:
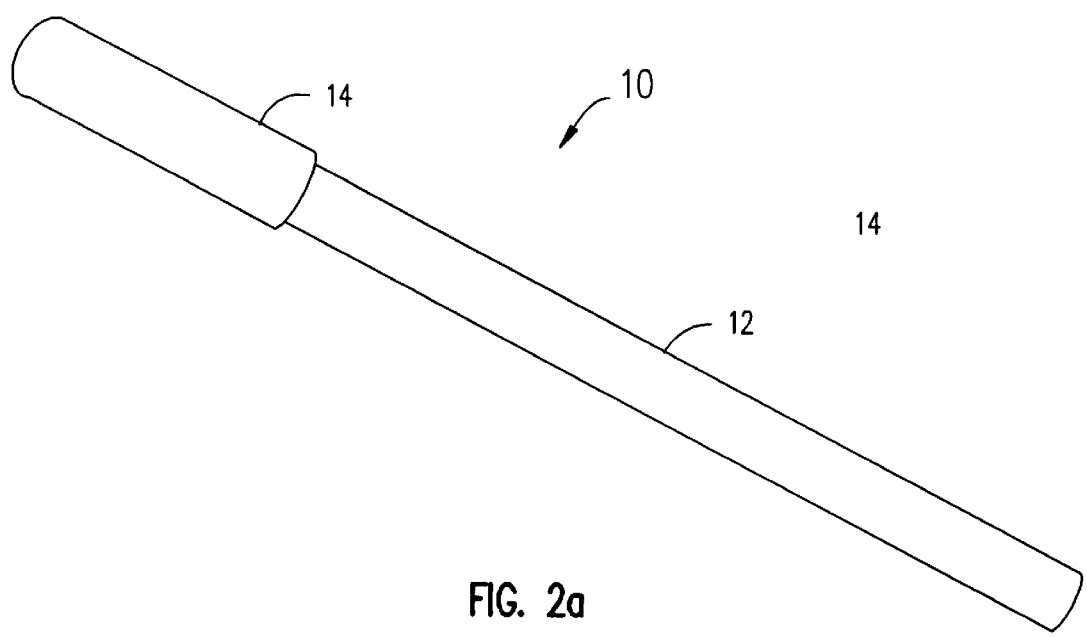
FIG. 2a is a perspective view of a second embodiment of the cleaning apparatus of the present invention.
Figure 2B:
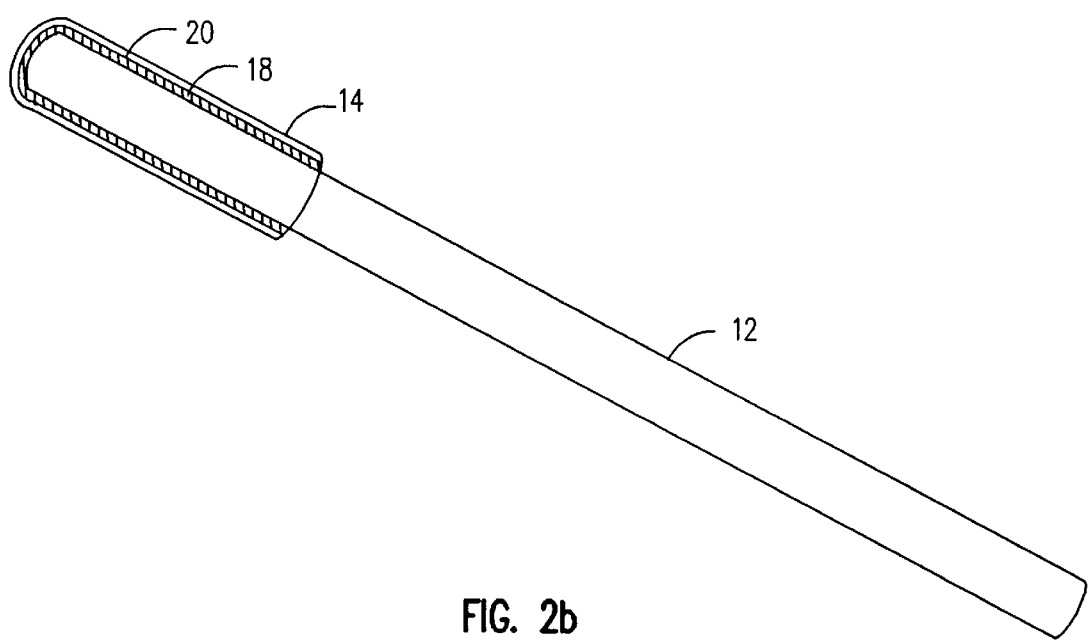
FIG. 2b is a side sectional view of the second embodiment of the cleaning apparatus of the present invention.

Referring now to FIGS. 2a and 2b, a second embodiment of the cleaning apparatus 10 of the present invention is shown. FIG. 2a is a perspective view of the second embodiment while FIG. 2b is a side view of the cleaning apparatus 10. Here, the adhesive material 20 described in connection with FIGS. 1a and 1b is applied over a more 10 compliant surface 18 such as a swab end to create the adhesive tip 14, which is suited for cleaning irregular surfaces by daubing.

Figure 3A:
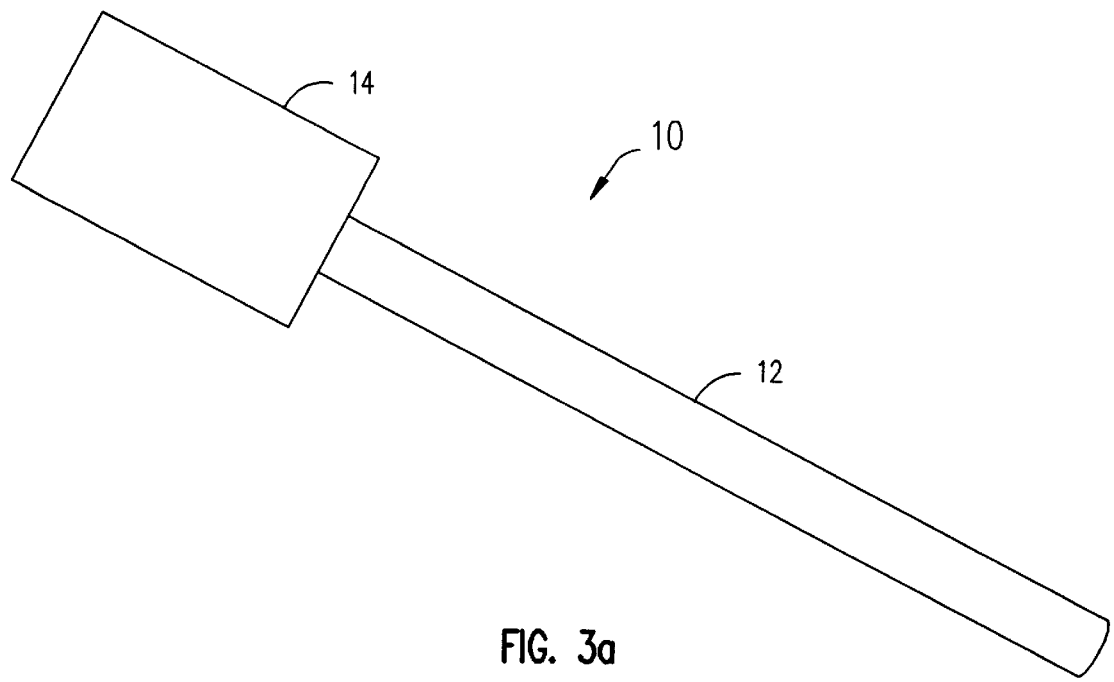
FIG. 3a is a perspective view of a third embodiment of the cleaning apparatus of the present invention.
Figure 3B:
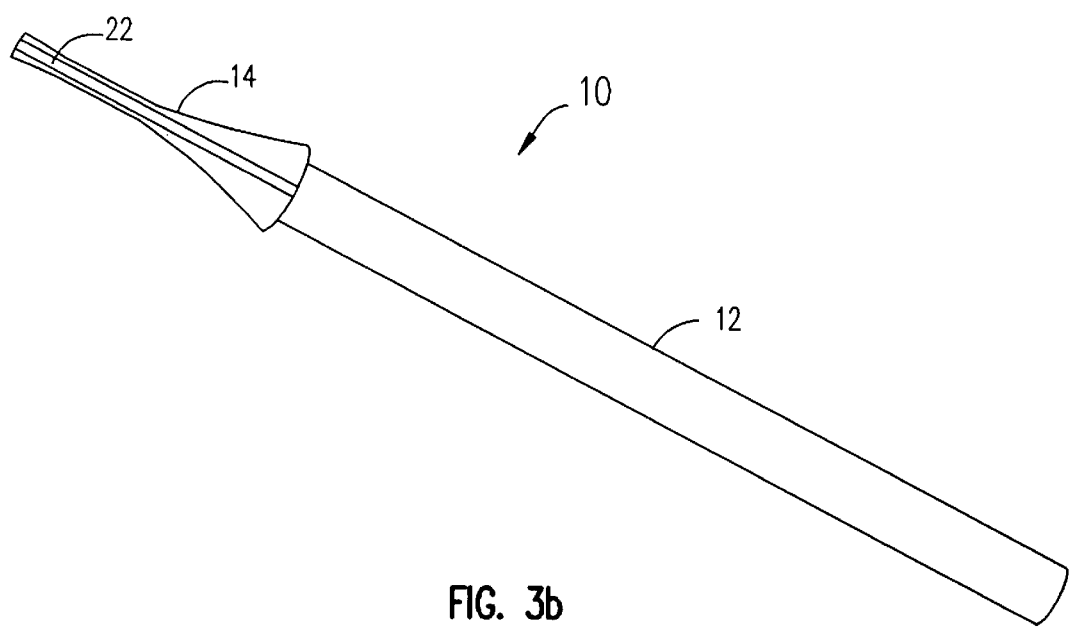
FIG. 3b is a side view of the third embodiment of the cleaning apparatus of the present invention.

Referring now to FIGS. 3a and 3b, a third embodiment of the cleaning apparatus 10 of the present invention is shown. FIG. 3a is a perspective view of the third embodiment while FIG. 3b is a side sectional view of the cleaning apparatus 10. Here, the adhesive tip 14 is formed with the adhesive film 20 described in connection with FIG. 1 being applied over a more resilient surface 22 such as a flat paddle for cleaning flat surfaces by daubing. With reference to FIGS. 2b and 3b, it can be seen that the adhesive film sticks to itself and easily stretches, conforming to any shape. It can be easily applied to numerous backing shapes and materials to meet the needs of the specific uses. Therefore, the embodiments shown in FIGS. 1 through 3 should be taken as exemplary and illustrative rather than limiting. In addition, the adhesive of the present invention may be applied directly to a substrate while it is still in a liquid, uncured state.

Figure 4:
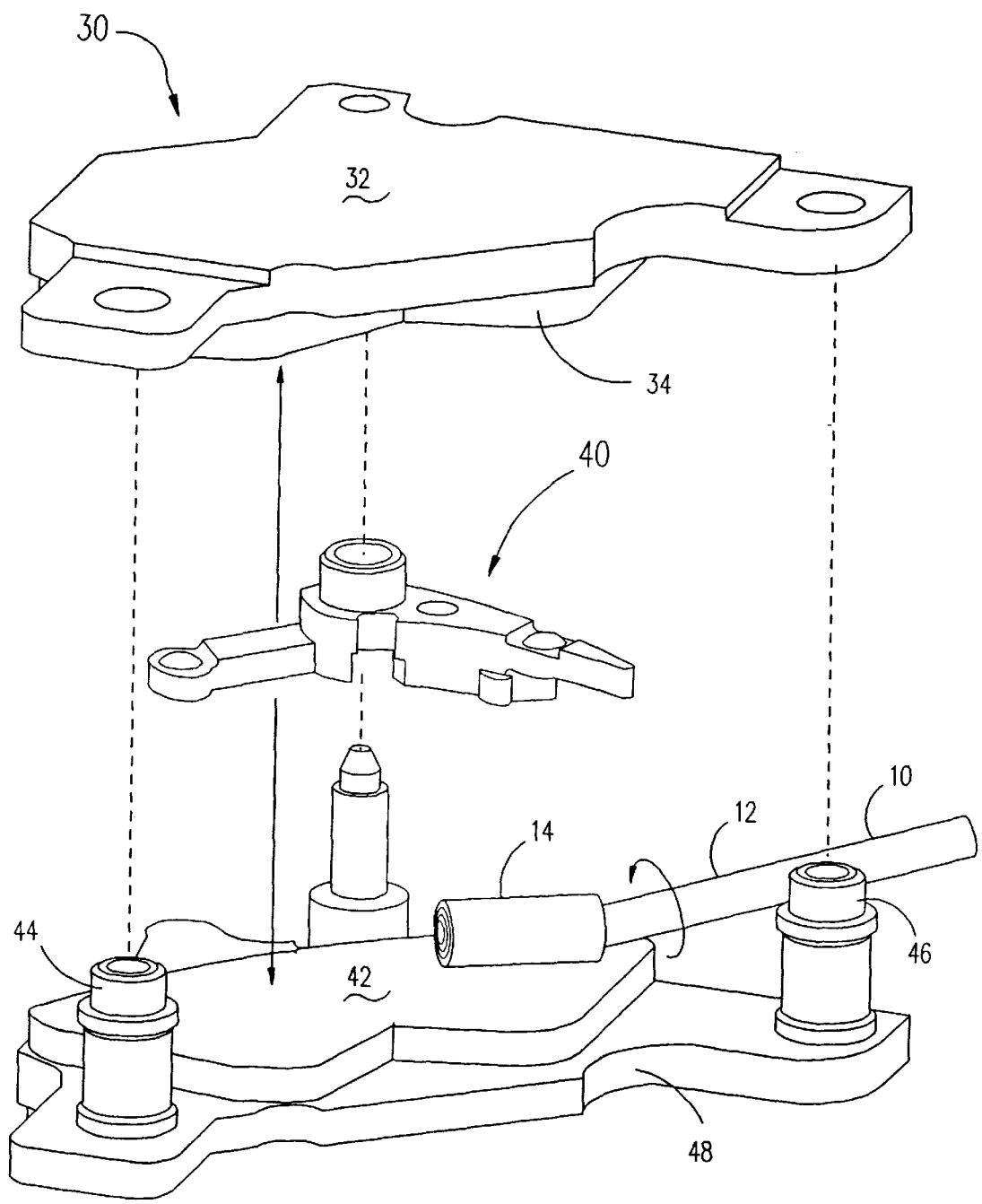
FIG. 4 illustrates one use of the cleaning apparatus of the present invention, showing the cleaning apparatus being used to clean the vcm assembly of a disk drive system.

FIG. 4 illustrates one use of the cleaning apparatus 10 of the present invention in the disk drive industry, showing the cleaning apparatus 10 being used to clean the magnets of a voice coil motor (VIC) assembly 30. Voice coil motor assembly 30 known in the disk drive arts, is comprised of a top plate 32 spaced above a bottom plate 48 with one or more magnets therebetween. Shown in FIG. 4 is a pair of magnets, 34 and 42. The top plate 32 and bottom plate 48 are spaced apart from each other by standoffs 44, 46 and actuator pivot latch 40. The vcm further includes an electrically conductive coil (not shown) disposed within a rearward extension of an actuator arm and between the top and bottom plates, while overlying the magnet in a plane parallel to the magnet. Although shown exploded in FIG. 4, a vcm assembly 30 in a small form factor disk drive system tolerates only the smallest of spacing between the upper 32 and lower 48 plates in the vcm assembly 30. Typically, these plates are only a few millimeters apart. The vcm is an especially susceptible to contamination during assembly of a disk drive system because ferromagnetic particles will stick to the vcm magnet(s) and thus have to be removed during rework. In FIG. 4, the cleaning apparatus 10 of the present invention is shown being inserted between the magnets and plates of the vcm assembly, where it can be rolled across the magnet surface to remove particles. However, the low residue and low out gassing properties of the adhesive do not leave contaminants behind that would further impact the operation of the drive.

Experimental data has shown the cleaning apparatus of the present invention provides a great improvement over the approaches taken in the prior art. For example, with regard to magnet cleaning of magnetic/iron particles, cleaning with a swab yields about a 5% to 10% cleaning efficiency, while the cleaning apparatus shows a 90% to 95% cleaning efficiency. For cleaning non-magnetic particles on a smooth surface, a swab yields about a 20% to 30% cleaning efficiency, while the cleaning apparatus shows a 90% to 100% cleaning efficiency. Lastly, for cleaning non-magnetic particles on an irregular surface, a swab yields about a 10% dry or 25% to 40%, when wet, cleaning efficiency, while the cleaning apparatus shows a 80% to 95% cleaning efficiency, when dry. The apparatus of the present invention is not limited to the use described herein, but rather is useful in the cleaning of any precision components where cleanliness is a key concern.

Figure 5:
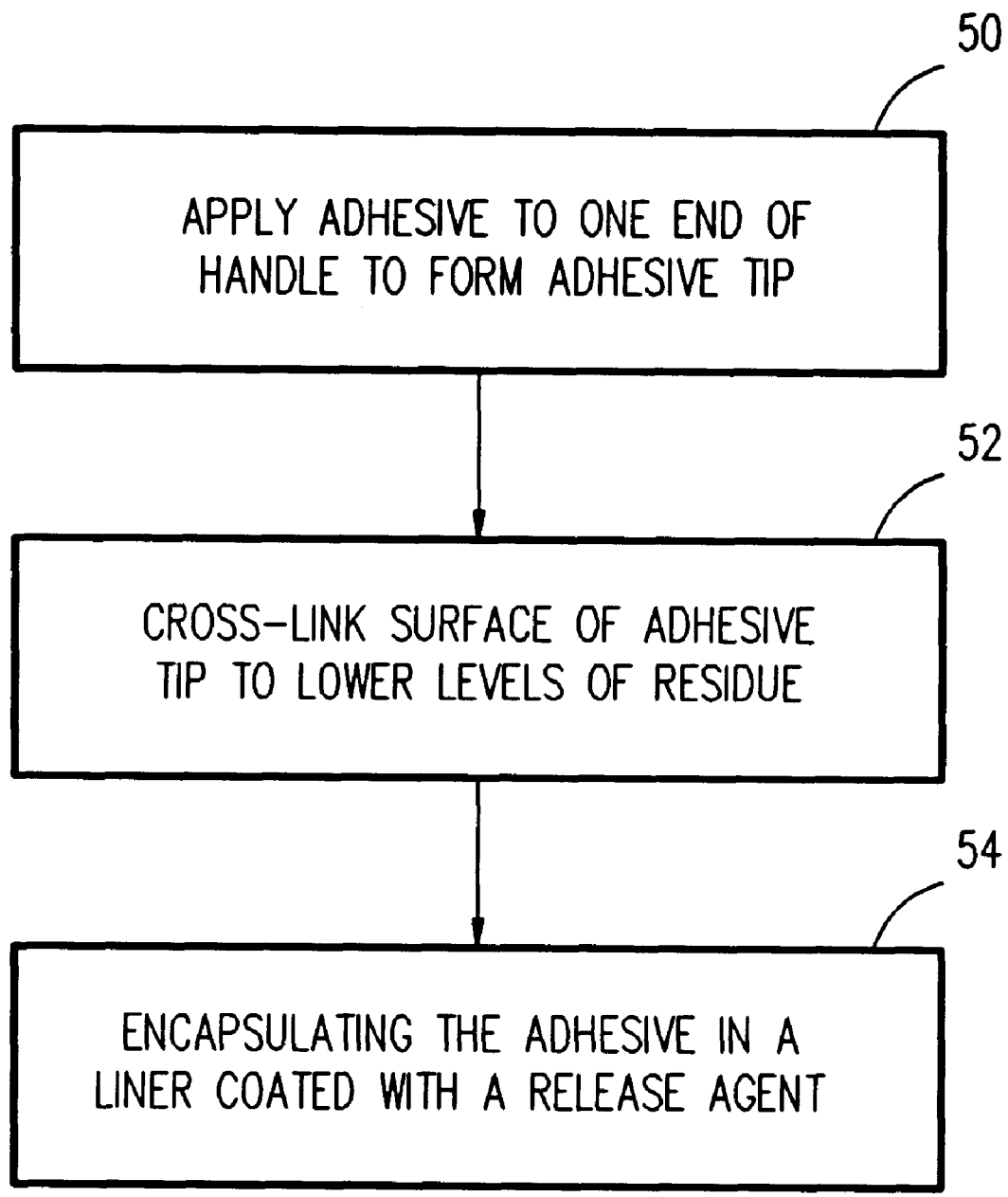
FIG. 5 is a flow diagram illustrating the steps of manufacturing the cleaning apparatus of the present invention.

Referring now to FIG. 5, a flow diagram of the method of manufacturing a cleaning apparatus of the present invention is shown and described. First, at step 50, the adhesive material 20 is applied to one end of the handle 12 forming the adhesive tip 14. As previously mentioned, the adhesive may be rolled about the end of the handle, formed over a shape on the end of the handle, or the handle may be immersed into a liquid, uncured version of the adhesive, and subsequently cured.

Next, at step 52, the surface of the adhesive tip i4 may be cross-linked to further reduce the residue levels. Cross-linking refers to the process whereby polymer molecules become attached to each other, reducing the probability that the molecules will remain on a surface with which they come in contact. The step is optional but would be practiced for certain applications. For example, the cleaning apparatus 10 of the present invention effectively cleans surfaces of difficult to remove particle contamination. A low outgassing, low residue adhesive is used to minimize organic outgassing and contact contamination, which is an important consideration for cleaning of sensitive parts such as those used in the disk drive and semi-conductor industries. However, for certain ultra-sensitive components, such as the air bearing surface (ABS) of magnetic recording heads, even lower residue levels may be necessary. In order to further reduce the contact residue levels of the cleaning apparatus, the surface of the adhesive on the adhesive tip 14 is cross-linked. In a preferred embodiment, this surface is cross-linked by exposing the surface to UV light, preferably with a significant content of 254 nm light and some 193 nm light. The process efficiency would increase if oxygen were removed from the irradiation environment, for example by purging with nitrogen. An alternative embodiment for cross-linking the surface of the adhesive tip 14 would use an e-beam to accomplish the cross-linking.

One example of cross-linking the adhesive surface using UV-light is as follows: Construct a Plexiglas container with an inlet for nitrogen and purge exit. Mount a 254/193 light source, for example a pen light, so the bulb sits horizontally above the adhesive surface. Purge with Nitrogen gas until the oxygen level is reduced to less than 20 ppm. Turn on the lamp and expose the adhesive until the surface is lightly cross-linked and no longer leaves a residue on the contacted surface.

Last, at step 54, the cleaning apparatus is encapsulated by a liner comprising typically of polyester coated with a clean release film to keep the adhesive tip clean prior to use. The release film must be free of transferrable siloxanes (methyl silicones) so that less than 0.1 nano gram per $cm^2$ siloxane is left as residue in the cleaning process.

While the present invention has been particularly shown and described with reference to the illustrated embodiments thereof, it will be understood by those skilled in the art that various changes in form and detail may be made without departing from the spirit, scope and teaching of the invention. Accordingly, the invention herein disclosed is to be considered merely as illustrative and limited in scope only as specified in the appended claims.

What is claimed is:

1. A cleaning apparatus comprising:
   an elongated handle;
   a compliant material disposed on one end of the handle; and
   an adhesive tip applied over the compliant material, said adhesive tip further comprising an adhesive material that has low residue and low outgassing properties so as to remove particles from surfaces of precision components without contaminating the components, and being a size adapted for use as a disk drive component cleaning apparatus.

2. The cleaning apparatus of claim 1, wherein the handle is formed of a rigid material.

3. The cleaning apparatus of claim 1, wherein the handle is formed of a flexible material.

4. The cleaning apparatus of claim 1, wherein the adhesive tip is further comprised an adhesive liquid cured about the end of the handle.

5. The cleaning apparatus of claim 1, wherein the adhesive tip is encapsulated in a liner coated with a release agent.

6. The cleaning apparatus of claim 1, wherein the low residue properties of the adhesive material further comprise having less than 0.1 $mg/cm^2$ residue from cleaning.

7. The cleaning apparatus of claim 1, wherein the adhesive tip has low transferable siloxane so that the adhesive tip leaves less than 0.1 nano gram per $cm^2$ siloxane residue on a surface it has cleaned.

8. The cleaning apparatus of claim 1, wherein the adhesive tip low residue property is such that the adhesive tip leaves less than 0.1 nano gram per $cm^2$ residue on a surface it has cleaned.

9. A cleaning apparatus comprising:
   an elongated handle:
   a compliant material disposed on one end of the handle; and
   an adhesive tip applied over the compliant material, said adhesive tip further comprising an adhesive material that has low residue and low outgassing properties, and being a size adapted for use as a disk drive component cleaning apparatus, wherein the adhesive tip is rotatably attached to the handle so as to allow axial rotation of said adhesive tip around said handle.

10. The cleaning apparatus of claim 9, wherein the low properties of the adhesive material has further comprise having less than 0.1 $mg/cm^2$ residue from cleaning.

11. A cleaning apparatus comprising:
    an elongated handle; and
    an adhesive tip disposed on one end of the handle, said adhesive tip further comprising an adhesive material that has low residue and low outgassing properties, and being a size adapted for use as a disk drive component cleaning apparatus, wherein the adhesive tip is rotatably attached to the handle so as to allow axial rotation of said adhesive tip around said handle, such that the adhesive tip can roll laterally across a surface when the handle is moved, and wherein the surface of the adhesive tip is cross-linked.

12. The cleaning apparatus of claim 11, wherein the adhesive material is further comprised of an adhesive film rolled about the end of the handle.

13. A cleaning apparatus comprising:
    an elongated handle; and
    an adhesive tip disposed on one end of the handle, said adhesive tip further comprising an adhesive material that has low residue and low outgassing properties so as to remove particles from surfaces of precision components without contaminating the components, and being a size adapted for use as a disk drive component cleaning apparatus, wherein the adhesive material is further comprised of an adhesive film formed over a flat, paddle shaped surface, wherein the surface of the adhesive tip is cross-linked.

14. The cleaning apparatus of claim 13, wherein the shaped surface is flexible.

15. The cleaning apparatus of claim 13, wherein the shaped surface is rigid.

16. The cleaning apparatus of claim 13, wherein the adhesive tip is encapsulated in a liner coated with a release agent.

17. The cleaning apparatus of claim 16, wherein the low outgassing properties of the adhesive material further comprise having an organic volatile outgassing of less than 0.5 percent.

18. The cleaning apparatus of claim 16, wherein the release agent is free of transferable siloxanes.

* * * * *